US 6,703,241 B1

(12) United States Patent
Sunshine et al.

(10) Patent No.: US 6,703,241 B1
(45) Date of Patent: Mar. 9, 2004

(54) REFERENCING AND RAPID SAMPLING IN ARTIFICIAL OLFACTOMETRY

(75) Inventors: Steven A. Sunshine, Pasadena, CA (US); Bruce Hermann, Winston Salem, NC (US); Beth C. Munoz, Vista, CA (US)

(73) Assignee: Cyrano Sciences, Inc., Pasadena, CA (US)

( * ) Notice: Subject to any disclaimer, the term of this patent is extended or adjusted under 35 U.S.C. 154(b) by 237 days.

(21) Appl. No.: 09/713,756

(22) Filed: Nov. 14, 2000

Related U.S. Application Data

(60) Provisional application No. 60/165,437, filed on Nov. 15, 1999.

(51) Int. Cl.[7] .............................................. G02N 31/00
(52) U.S. Cl. .............................. 436/8; 436/2; 436/147; 436/148; 73/23.2; 73/23.21
(58) Field of Search ........................ 436/2, 8, 62, 147, 436/148, 149, 150, 174; 73/23.2, 23.21, 23.22, 23.23, 23.3, 23.32

(56) References Cited

U.S. PATENT DOCUMENTS

| | | | | |
|---|---|---|---|---|
| 5,169,235 A | * | 12/1992 | Tominaga et al. | 374/129 |
| 5,261,411 A | * | 11/1993 | Hughes | 128/668 |
| 5,571,401 A | | 11/1996 | Lewis et al. | 205/787 |
| 5,698,089 A | | 12/1997 | Lewis et al. | 205/787 |
| 5,788,833 A | * | 8/1998 | Lewis et al. | 205/787 |
| 6,060,327 A | | 5/2000 | Keen | 436/518 |
| 6,085,576 A | | 7/2000 | Sunshine et al. | 73/29.01 |
| 6,129,673 A | * | 10/2000 | Fraden | 600/474 |
| 6,377,840 B1 | * | 4/2002 | Gritsenko et al. | 600/476 |
| 6,463,393 B1 | * | 10/2002 | Giger | 702/97 |

* cited by examiner

*Primary Examiner*—Jill Warden
*Assistant Examiner*—Dwayne K Handy
(74) *Attorney, Agent, or Firm*—Townsend and Townsend and Crew LLP

(57) ABSTRACT

Devices and methods are disclosed that are effective to produce reliable vapor measurements in the presence of drift. In certain instances the sensor module is mounted externally on a housing. In other instances, the sensor module contains a first sensor element incorporating a first array of sensors and a second sensor element incorporating a second array of sensors wherein both sensor elements are mounted externally on the housing. In other embodiments, the present invention relates to mapping an x-y surface for detection of an analyte, the method includes moving in tandem at least two sensor arrays separated by a distance "d" across an x-y surface to produce a plurality of responses and analyzing the responses to map the x-y surface for detection of an analyte. Moreover, the present invention provides a sensor module, such as in a handheld device, comprising at least two pneumatic vapor paths and at least two sensor arrays. The dual pneumatic train allows rapid sensing as it increases the duty cycle frequency.

14 Claims, 8 Drawing Sheets

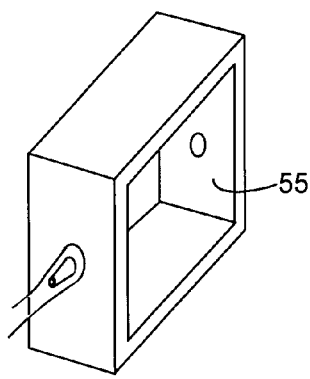
FIG. 6B
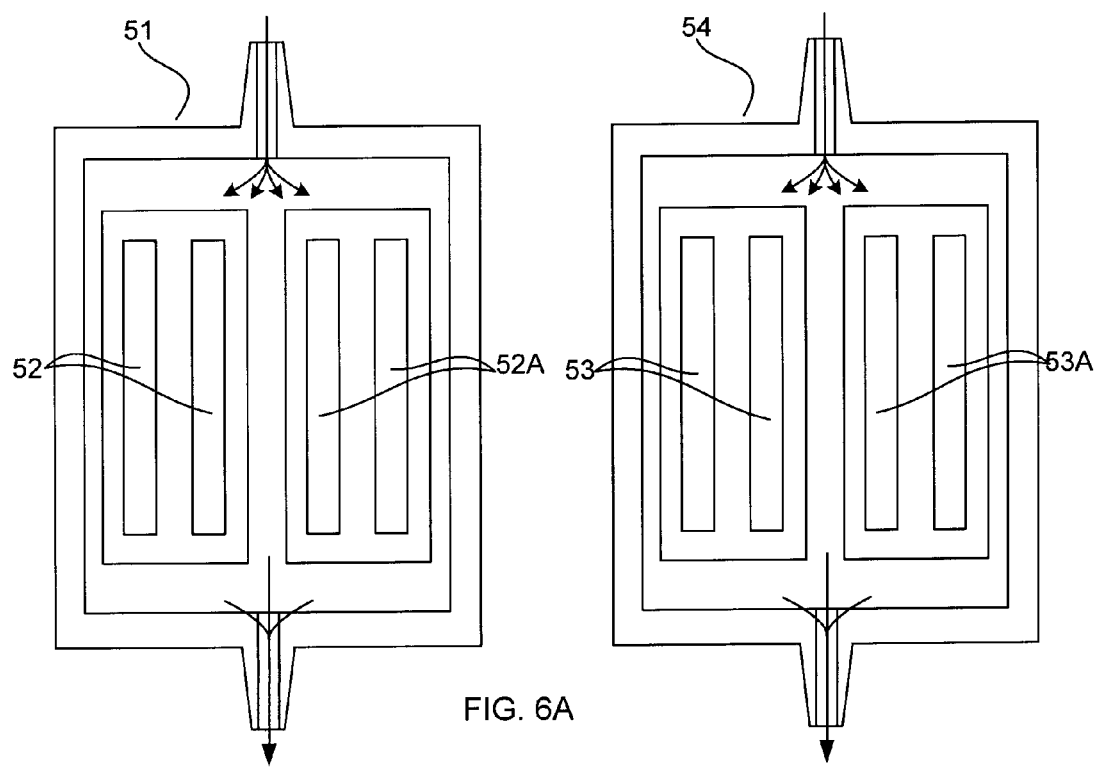
FIG. 6A
FIG. 6

REFERENCING AND RAPID SAMPLING IN ARTIFICIAL OLFACTOMETRY

CROSS REFERENCE TO RELATED APPLICATIONS

This application claims priority to U.S. Provisional Patent Application No. 60/165,437, filed Nov. 15, 1999, the teaching of which incorporated herein by reference in its entirety for all purposes.

FIELD OF THE INVENTION

In general, this invention relates to chemical sensing, and in particular, to referencing, rapid sampling and methods of reducing or eliminating drift in artificial olfactometry.

BACKGROUND OF THE INVENTION

An electronic nose is an array of chemical sensors coupled with computerized multivariate statistical processing tools. These sensors respond to a wide variety of analytes giving rise to a unique signature or pattern for a given analyte. The pattern is interpreted using pattern recognition algorithmns to identify or quantify the analyte of interest.

In general, the chemical sensors are based on physical or chemical absorption, chemical desorption or optical properties that take place on the sensors. Suitable sensor types include metal oxide semiconductors, metal oxide semiconducting field effect transistors, conducting organic polymers, quartz microbalance, surface acoustic wave devices and conducting and nonconducting regions sensors.

For the analysis of organic solvent vapors, certain devices, such as surface acoustic wave devices, respond to the extent of vapor sorption. This sorption is typically rapid, reversible and is proportional to vapor concentration. However, various drawbacks exist. For example, certain sensors are susceptible to humidity, have low confidence limits, are susceptible to drift and are unstable. In certain instances, instability can be corrected using background subtraction techniques. Humidity in the vapor can be eliminated by using a preconcentrator with water vapor absorbents. Confidence limits can be enhanced by using a limit of recognition that is defined as the concentration below which a vapor can no longer be reliably recognized from its response pattern (see, Zellers et al., *Analytical Chemistry*, 70, 4191–4201 (1998)).

Drift is one of the most serious drawbacks of sensor technology. Drift is defined as the temporal shift of sensor response under constant or static conditions. The reason for certain types of drift is not well understood, but it is believed to result from unknown dynamic processes. Temperature or pressure fluctuations, or changes in the sensing environment can also cause drift. When the reasons for drift are known, it is sometimes possible to develop mathematical models that can compensate for its effects (see, Semin et al., *Meas. Techn.* 38, 30–32 (1995)). Work has been done on ways to improve the stability of sensors; however, it is not yet possible to fabricate sensors with no drift at all.

One possible solution to the effects of drift is to use a reference gas (see, Fryder et al. *Transducers '95 and Eurosensors IX.*, Stockholm Sweden, pp. 683–686 (1995)). This technique is difficult or impractical in some situations, such as a handheld sensing device. Another technique is the use of a theory of hidden variable dynamics for the rejection of common mode drift. Moreover, the hidden variable approach can be couple with adaptive estimation methods to compensate for drift (see, Holmberg et al., *Sensors and Actuators* B 42, 285–294 (1997)).

In view of the inherent instability of certain sensor arrays, there remains a need to have effective referencing and calibration in spite of the presence of drift. Devices and methods are needed which effectively produce reliable vapor measurements in the presence of drift. The present invention fulfills these and other needs.

SUMMARY OF THE INVENTION

Temporal shift of sensor response under constant conditions is one of the most serious drawbacks of sensor technology. Devices and methods are needed which are effective to produce reliable vapor measurements in the presence of temporal shift.

As such, in certain aspects, the present invention provides a method for reducing drift in an artificial olfaction device having an array of sensors, the method comprising: contacting the array of sensor with an analyte at a first temperature to produce a first response; contacting the array of sensor with the analyte at a second temperature to produce a second response; and subtracting the first response from the second response thereby reducing drift in the sensor array. In certain instances, the artificial olfaction device is a handheld device.

In another embodiment, the present invention provides a sensor module configured for external mounting on a sensing apparatus for detecting an analyte in a fluid, the sensor module comprising: a casing sized and configured to be received in a receptacle of the sensing apparatus; at least two sensor to provide a distinct response when exposed to one or more analytes located within the sample chamber; and an electrical connector configured to be releasably engageable with a mating electrical connector of the sensing apparatus when the sensor module is received in the receptacle, the electrical connector transmitting the characteristic signals from the at least two sensor to the sensing apparatus.

In yet another embodiment, the present invention provides a sensing device for detecting an analyte, comprising: a housing; a first sensor element incorporating a first array of sensors and a second sensor element incorporating a second array of sensors wherein both sensor elements are mounted externally on the housing. In certain embodiments, the first sensing element is designed to sense a vapor, and is referred to as the sensing element. The second sensor element is designed as a reference for the device and is referred to as the referencing element. In certain aspects, a physical barrier exists between the reference sensor element and the analyte to be identified. Preferably, the reference element is pasivated with a material to prevent the analyte from contacting the surface of the reference element.

In still yet another embodiment, the present invention provides a sensing device for detecting an analyte, comprising: a housing; a sensor module mounted externally on the housing and incorporating an array of sensors, each of the sensors providing a different response in the presence of the analyte; a monitoring device mounted on the housing and configured to monitor the responses of the array of sensors incorporated in the sensor module, and further configured to produce a corresponding plurality of sensor signals; and an analyzer mounted on the housing and configured to analyze the plurality of sensor signals to identify the analyte.

In still other embodiments, the present invention relates to mapping an x-y surface for detection of an analyte, the method comprising: moving in tandem at least two sensor arrays separated by a distance "d" across an x-y surface to produce a plurality of responses; analyzing the responses and thereby mapping the x-y surface for detection of an analyte. In certain preferred embodiments, the tandem sensor system resides on a x-y translational stage.

In yet another embodiment, the present invention provides a sensor module, such as in a handheld device, comprising at least two pneumatic vapor paths and at least two sensors arrays. The dual pneumatic train allows rapid sensing as it increases the duty cycle frequency.

These and other aspects of the present invention will become more apparent when read with the detailed description and figures that follow.

BRIEF DESCRIPTION OF THE DRAWINGS

FIGS. 6A–B illustrate Panel 6A a top sectional view of an embodiment of the present invention and Panel 6B a module cover embodiment.

DETAILED DESCRIPTION OF THE INVENTION AND PREFERRED EMBODIMENTS

I. DEVICES

A. Externally Mounted Sensor Module

In certain aspects, the present invention provides a sensing device for detecting an analyte, comprising: a housing; a sensor module mounted externally on the housing comprising an array of sensors, each of the sensors providing a response in the presence of the analyte; a monitoring device mounted on the housing and configured to monitor the responses of the array of sensors incorporated in the sensor module, further configured to produce a corresponding plurality of sensor signals; and an analyzer mounted on the housing and configured to analyze the plurality of sensor signals to identify the analyte.

Preferably, the sensor module is capable of automatic physical movement. The physical movement is controlled by a controller that is configured to control the sensor module. This automatic physical movement of the sample module allows referencing of the sensor arrays. For instance, the sensor module is placed in a first position to be calibrated. The first position does not expose the sensor array to the test area or sample containing the analyte. Thus, the first position is a calibration position wherein the sensor response is set to a null value. After the sensor array is calibrated or nulled, the sensor module is automatically moved closer to the test sample or area containing the vapor or analyte to be measured. Sampling of the vapor is quick and reliable, and because the sensor module is externally mounted, the response of the sensor array is not impeded by sensor array pneumatics. As will be apparent to those of skill in the art, although the sensor array is set to a null value, it is possible that some background signal exists.

Figure 1:
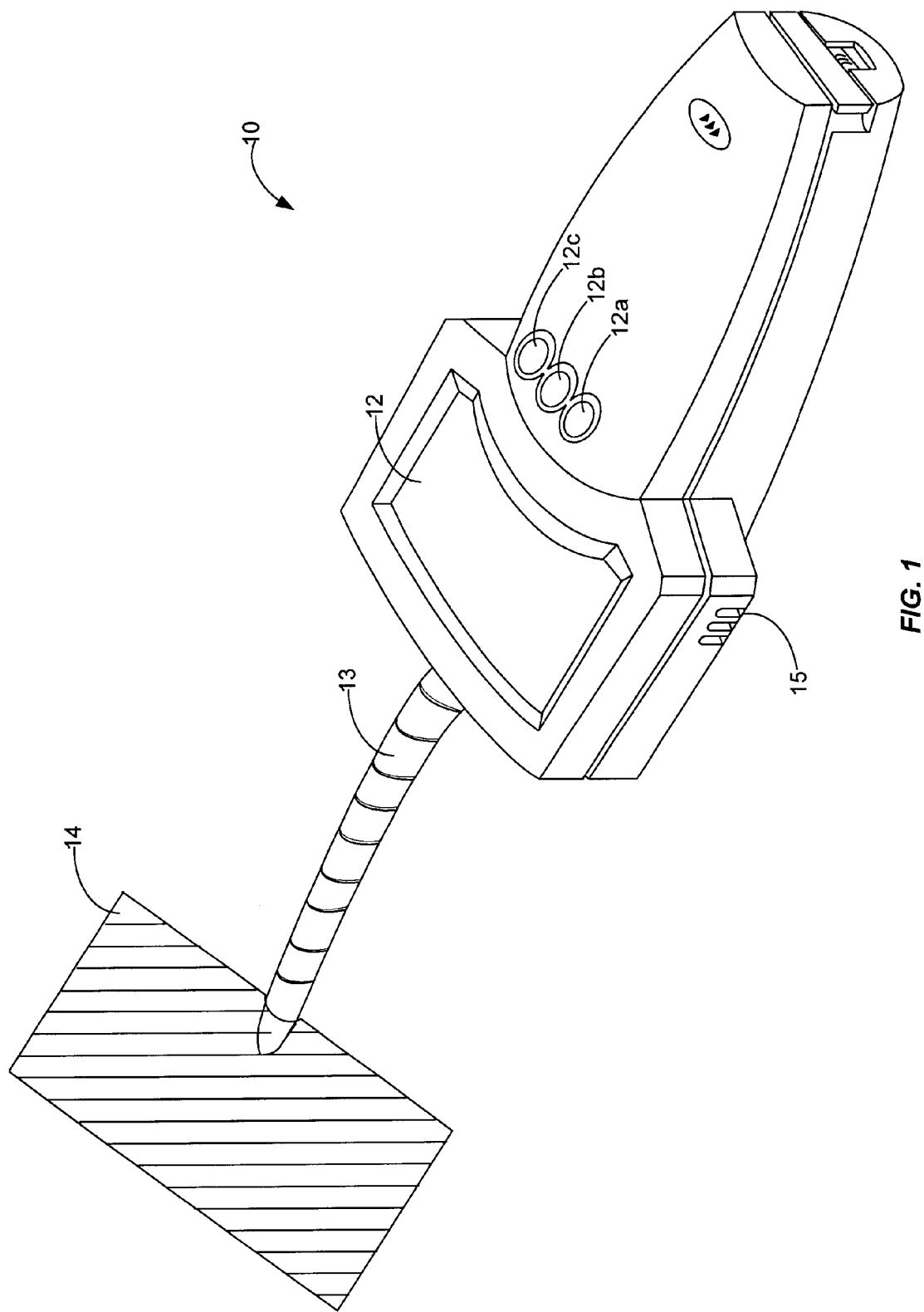
FIG. 1 illustrates a top perspective view of an embodiment of an electronic nose device of the present invention.

In an especially preferred embodiment, the externally mounted sensor is on a handheld electronic nose. As shown in FIG. 1, the sensor module is externally mounted. FIG. 1 shows a top perspective view of an embodiment of a handheld device. The handheld device includes an elongated housing having a lower end sized to be conveniently grasped and supported by the hand of an operator. A display 12 and several push-button control switches 12a through 12c are located on the housing's topside, for convenient viewing and access by the operator. Push-buttons 12a–c can be used to control the device during its various operating modes. Display 12 displays information about such operating modes and the results of the device's sensing and fluid detection. As use herein, a fluid is a unit of a vapor, liquid, solution, gas, or other forms, and mixtures thereof, of a substance being analyzed. Thus, a fluid sample can include chemical analytes, odors, vapors, and others. The sample can comprise a single analyte or a plurality of analytes.

A tubular wand 13 having an externally mounted sensor 14 and an exhaust port 15 are provided to respectively receive and discharge samples to be analyzed. In certain embodiments, the externally mounted sensor is a plug-in sensor module. The operation of electronic circuitry of sensor modules, similar to the externally mounted sensor module of the present invention, is described in detail in U.S. Pat. No. 6,085,576, issued Jul. 11, 2000, to Sunshine et al. and incorporated herein by reference.

In one embodiment, the externally mounted sensor module of the present invention incorporates "swap and sniff" technology. Advantageously, the externally mounted modules can be easily swapped to compensate for various analytes or for specific environmental conditions. In certain aspects, a sensor module is configured to be releasable engageable into an external portion of a handheld device.

The sensor module includes a casing having at least two sensors and an electrical connector. The casing is sized and configured to be received in an external receptacle of the sensing apparatus. The electrical connector is configured to be releasably engageable with a mating electrical connector of the sensing apparatus when the sensor module is received in the receptacle. The electrical connector transmits the characteristic signals from the sensors to the sensing apparatus. In certain embodiments, the characteristic sensor parameters and data are stored in a memory devices such as an electrically programmable ROM (EPROM), an electrically erasable and programmable PROM (EEPROM), and other memory technologies, integrated in the sensor module. As will be apparent to those of skill in the art, the externally mounted sensors does not preclude the presence of an internally mounted sensor.

In certain aspects, the sensor module contains a heating element. An on-board processor can be used to provide temperature control for each individual sensor array device in the sensor module. In one implementation, each sensor array device can include a backside heater. Further, the processor can control the temperature of the sample chambers either by heating or cooling using a suitable thermoelectric device. Moreover, the analyte vapor can be heated and cooled within strict temperature limits.

Figure 2:
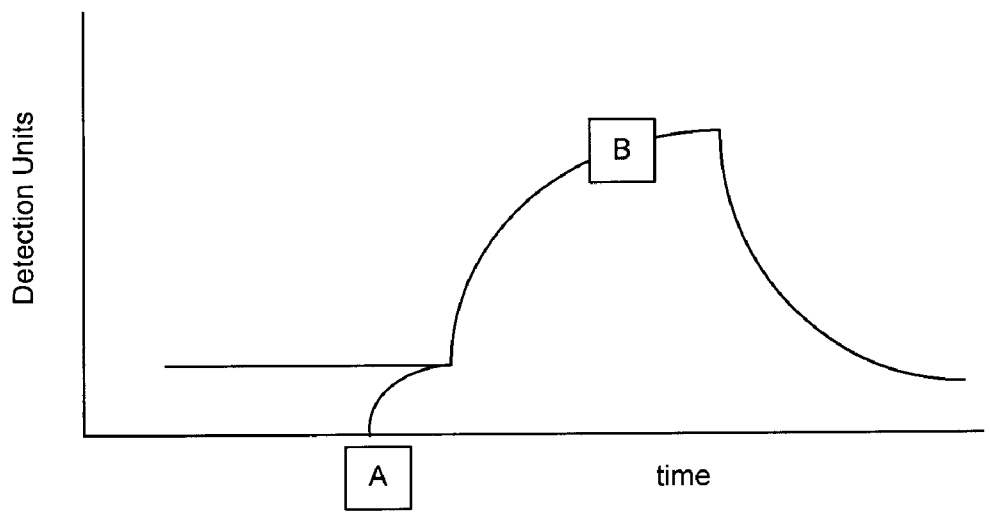
FIG. 2 illustrates a sensor response using a device of the present invention.

As illustrated in FIG. 2 the response of a sensor array using the foregoing movable or retractable sensor module embodiment is shown. At point "A", the sensor module is away from the sample in a first position. The sensor module is then placed in a second position, wherein the sample module is over the sample or area to be tested and the sensor responds (point "B"). Thereafter, the sensor is moved back to the first position. Using this configuration for a sensing device, it is possible to take advantage of the decrease in concentration as a function of distance to calibrate or reference the sensing device. With reference to FIG. 1 for example, the tubular wand 13 having an externally mounted sensor 14 can be telescopically retracted to provide the first position. In the fully retracted position the sensor module is in the first position. In the fully extended position the sensor module is in the second position.

B. Externally Mounted Sensor Module Having Two Sensor Elements

In another aspect, the present invention provides a sensing device for detecting an analyte, comprising: a housing; a first sensor element incorporating a first array of sensors and a second sensor element incorporating a second array of sensors wherein both sensor elements are mounted externally on a housing. In certain embodiments, the first sensing element is designed to sense a vapor, and is referred to herein as the sensing element. In certain aspects, the second sensor element is designed as a reference, and is referred to herein as the referencing element. In a preferred aspect, the first sensor element is a first array of sensors and the second sensor element is a second sensor array, wherein the first and second sensor arrays comprise sensors that are compositionally similar or the same. As will be apparent to those of skill in the art, the externally mounted sensors does not preclude the presence of an internally mounted sensor.

Figure 3:
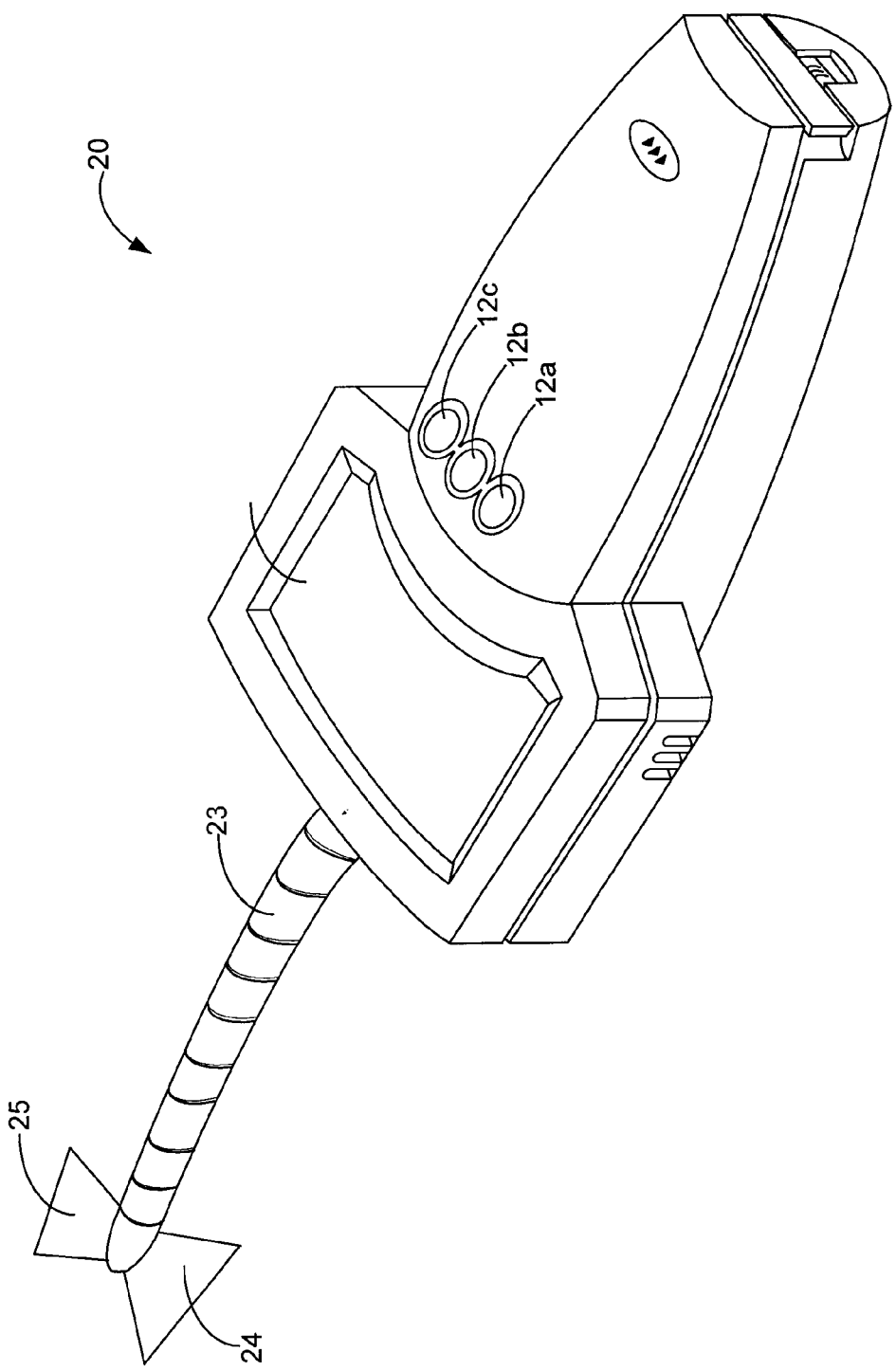
FIG. 3 illustrates a top perspective view of an embodiment of an electronic nose device of the present invention.

As shown in FIG. 3, the artificial olfaction device 20 has a tubular wand 23 that has an externally mounted first sensor module 24 and an externally mounted second sensor module 25. Preferably, the first sensor module comprises a sensor array and the second sensor module comprises a sensor array having similar or the same sensor type. For example, if sensor element in 24 comprises surface acoustic wave sensors, the referencing sensor element in 25 will also comprise surface acoustic wave sensors. In this manner, both the first sensor element and the second sensor element have similar or the same sensor type.

In other aspects, the device comprises two sensor elements that are externally mounted, wherein the second sensor element is positionally located differently (e.g., further away from the object to be measured) than the first sensor element. In this aspect, a vapor concentration gradient exists to provide a "reference" and a real measurement. The first sensor element closest to the sample provides the real measurement. The second sensor element, i.e., the reference sensor element, is located further away from the object to be measured and thus provides a reference.

In a further aspect, the present invention provides a device having two sensor elements wherein the location of the two sensors and differential vapor detection can be used for analyte determination. For instance, two sensors i.e., sensor element 1 and sensor element 2, can be separated by some distance, "d," and if the vapor at point 1 is different than at point 2 (point 1 and point 2 are separated by distance "d") there will be a differential response between sensor element 1 and sensor element 2. This differential response can be used to reference the two sensors with respect to drift.

In addition to referencing, the sensors can be used to advantageously map a surface, such as a planar surface. For example, if the two sensors are separated by 1 inch i.e., "d"=1 inch, and one sensor is placed over the test sample and the other sensor is not over the test sample, this will create a differential signal. However, if both sensor elements are over a test sample or not over a test sample, the differential reading will be close to zero. This differential response is useful for mapping a surface. If the objective is to locate contamination on a surface, for example, a countertop, dirty floorboards, hazardous leaks, fecal matter, anywhere there is a point source having a chemical profile, the edge of the contamination will signal a positive response. This is advantageous because any deviation indicates a response. In general, a deviation from a zero response is typically more sensitive than trying to see a small change on a large baseline.

As such, in certain embodiments, the present invention relates to mapping an x-y surface for detection of an analyte, the method comprising: moving in tandem at least two sensor arrays separated by a distance "d" across an x-y surface to produce a plurality of responses; analyzing the responses and thereby mapping the x-y surface for detection of an analyte. In this embodiment, the two sensor arrays are separated by a distance "d". If one sensor array is placed over an analyte, the analyte being on the x-y surface, and the other sensor is not over the analyte, this will create a differential signal between the sensor arrays. However, if both sensor arrays are over the analyte or, alternatively, not over the analyte, the differential reading will be small or close to zero. The resolution of the analyte on the x-y surface is inversely proportional to the distance "d". The greater the resolution required, the smaller the distance separating the tandem sensor array.

Using the methods of the present invention, it is also possible to increase the dynamic range of the sensor arrays. The dynamic range is characterized by the lowest detectable amount of analyte, which is given by the noise of the sensor response, and the maximum detectable amount of analyte that is given by the saturation effects of the sensor. Using the devices of the present invention, it is possible to reduce the noise level of the sensor system thereby increasing the dynamic range of the sensor arrays.

C. Pneumatics

Figure 4:
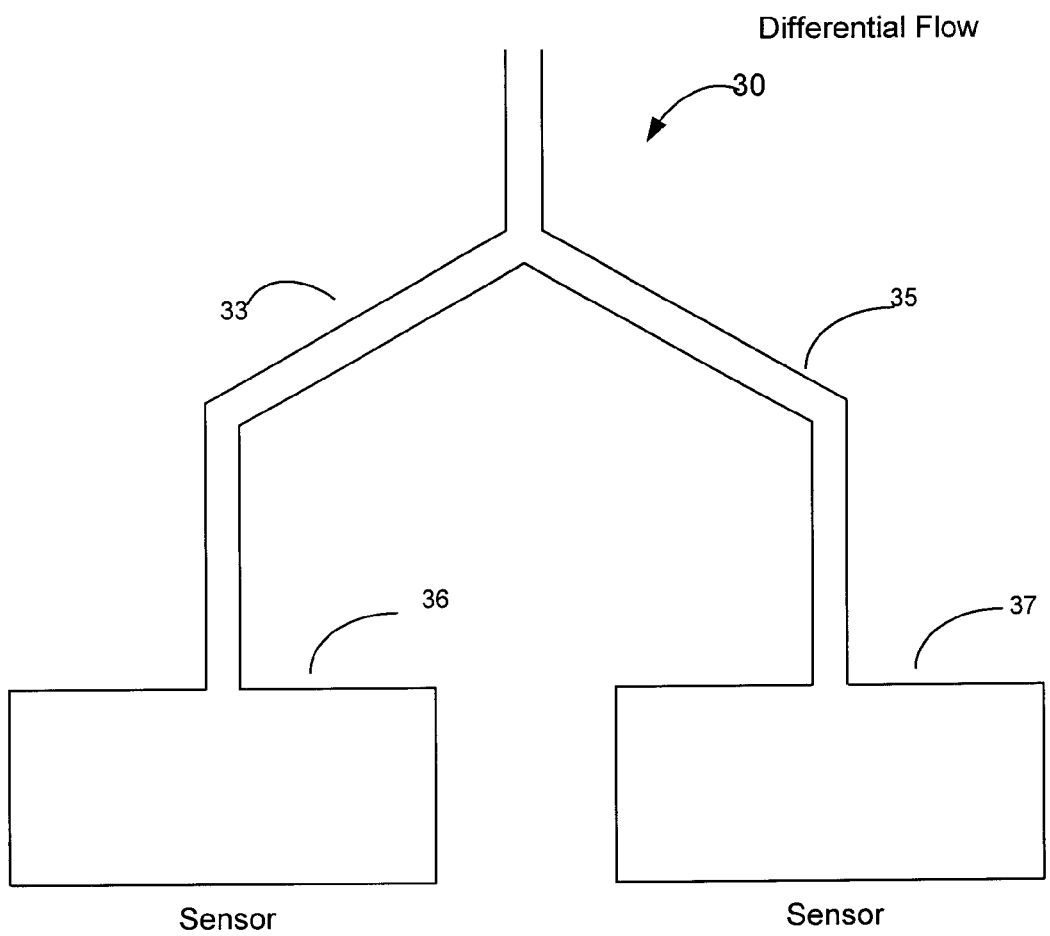
FIG. 4 illustrates differential flow pneumatics of the present invention.

As shown in FIG. 4, in certain embodiments, the present invention relates to an increased duty-cycle pneumatic sensing train 30. In a preferred embodiment, the sensor module comprises at least two pneumatic vapor paths 33, 35 and at least two sensor arrays 36, 37. In a preferred differential flow pneumatic train 30 of the present invention, sensors 36, 37 can be independently externally mounted, internally mounted, or alternatively, one sensor can be externally mounted and one sensor can be internally mounted.

In operation, sensor 36 is used to detect an analyte. While sensor 36 is being purged, sensor 37 can be used for detection or vise versa. Using the differential flow pneumatics of the present invention, it is possible to increase the frequency of analyte detection. In certain other embodiments, the pneumatics permits switching between a calibration source and an analyte source. Where sensor calibrations are frequent, the module of the present invention provides the ability to switch gases on a schedule consistent with desired pre-programmed calibration cycles.

In a further aspect, the present invention relates to sensor pneumatics comprising a pump having a reverse flow feature. The pump functions in alternative modes wherein in the first mode, sample air is taken in, and in a reverse mode, background air purges the system. In this manner, the duty cycle can be increased over conventional pumps.

D. Pasivasion Layer

In other embodiments, the present invention provides a sensing device comprising a first sensor element and a second sensor element that are physically located in spatially similar or identical positions with regard to the analyte; however, the analyte is prevented or blocked from contacting the second sensor element (i.e., the reference sensor). In this embodiment, a physical barrier exists between the reference sensor element and the analyte to be identified. Preferably, the sensing element is pasivated with a material to prevent the analyte from contacting the surface of the sensing element. Suitable pasivation materials include, but are not limited to, $SiO_2$ and $SiO_2$ based films, thermal oxides, silane, $SiH_4$, $Si_3N_4$, tetraethoxysilane, $Si(OC_2H_5)_4$, boro silicate glasses, and spin on glass.

Figure 5:
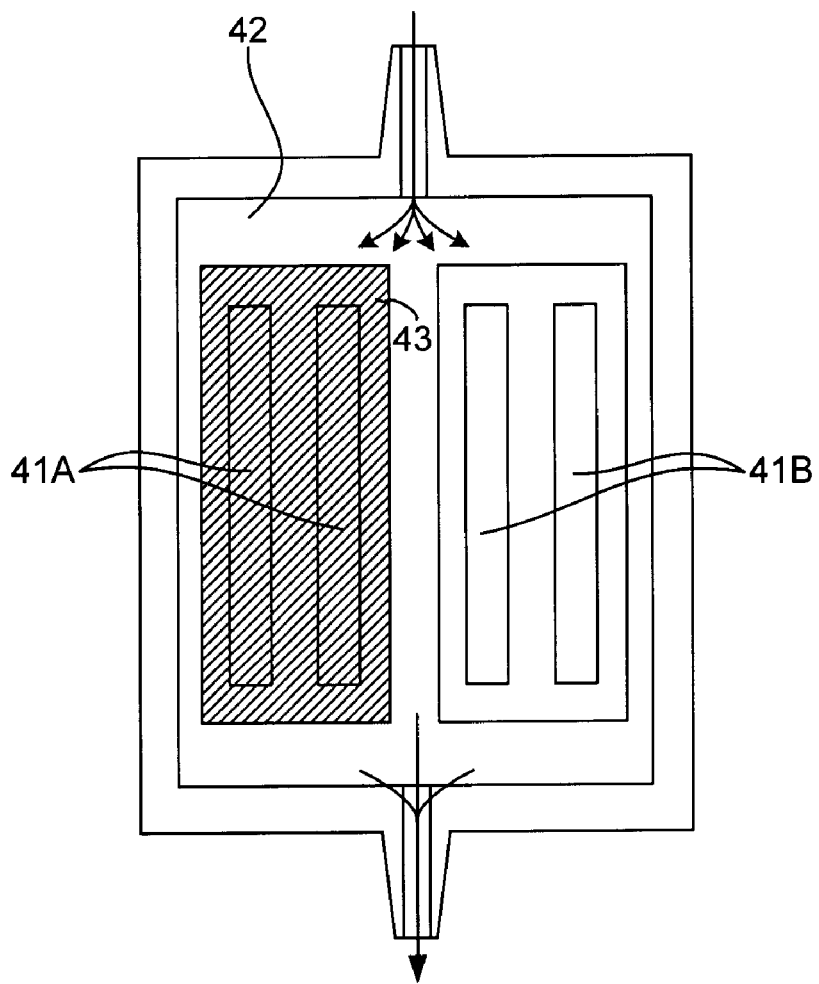
FIG. 5 illustrates a top sectional view of an embodiment of the present invention.

FIG. 5 shows a top sectional view of an embodiment of a sensor module that includes four plug-in sensor devices 41A and 41B within a single cavity or sample chamber 42. Disposed atop sensor array 41A is a pasivation layer 43 (hatched lines) to prevent or block the analyte from contacting sensor array 41A.

In another embodiment, the sensing device is configured so vapors do not contact the surface of the second sensor element i.e. the reference element. This can be accomplished by the use of a second sensor module. The reference-sensing module completely encloses the reference sensors, thereby preventing vapors to contact the surface of the sensors. With regard to FIG. 6, a top sectional view of an embodiment having two modules 51 and 54 wherein the first module is a sensing module 51 that includes 2 plug-in sensor devices 52 and 52A. The second sensing element 54 is a referencing element and also includes 2-plug-in sensor devices 53 and 53A. Sample chamber 54 is defined, in part, by a cover 55 (FIG. 6B) that is secured over module 54.

In another aspect, the reference element has a porous membrane associated therewith. In this way, the analyte's contact with the sensor array is slowed. The porous membrane limits diffusion to the reference sensor. This process of limited diffusion of the analyte allows sampling of the sensors at different points of time and thus, referencing and calibration can be done simultaneously. The sensors are identical and thus the responses are identical. The pasivation material only slows diffusion and is not analyte selective. Suitable porous pasivation layers include, but are not limited to, porous plastics, Teflon, and dialysis materials.

Moreover, the pasivation layer can reduce or eliminate humidity. Using an absorption or adsorption material especially designed for water vapor, the pasivation layer can reduce or eliminate humidity in the test sample.

E. Methods to Reduce Drift

Figure 7:
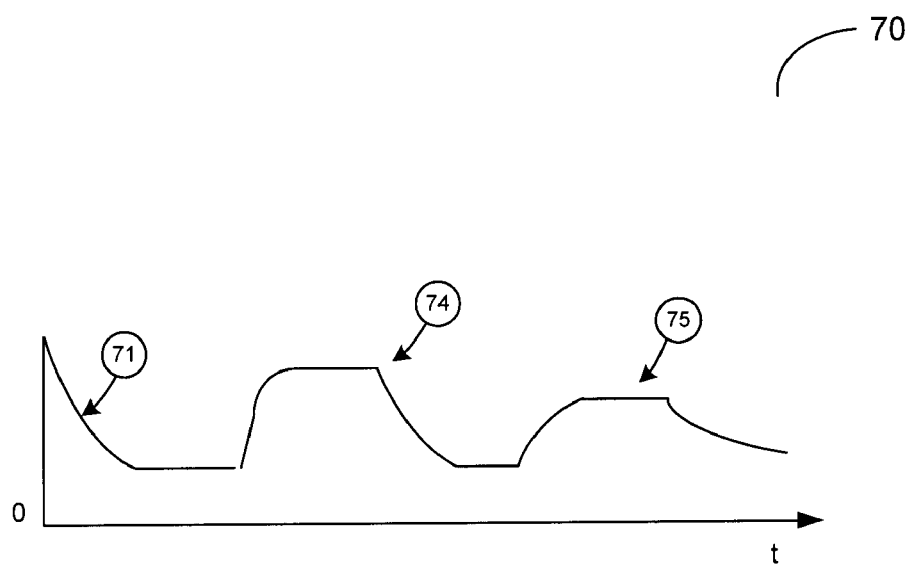
FIG. 7 illustrates drift in sensor arrays.

Instabilities and drift are serious problems in chemical sensors and could effect the identification of analytes. Non-cumulative drift denotes statistical variations of the sensor signal or response. Cumulative drift leads to irreversible changes of calibration and can result from sensor deterioration. FIG. 7 is an xy plot 70 of sensor signal versus time. Short-term drift can occur after switching on the sensor array device 71. These short-term drifts are caused by the time required to establish steady-state conditions, such as a constant operational temperature of the sensor array. In certain instances, thermal drift is related to changes of the sensor signal upon variations of ambient temperature. Sensor signals 74 and 75 show actual analyte sensing. Thermal drift can be reduced or eliminated by maintaining the sensor module at a uniform temperature. It is possible to reduce, compensate or eliminate drift using differential temperature measurements.

As such, the present invention provides a method for reducing drift by using differential thermal measurements. Thus, in another embodiment, the present invention provides a method for reducing drift in an array of sensors, comprising: contacting the array of sensor with an analyte at a first temperature to produce a first response; contacting the array of sensor with the analyte at a second temperature to produce a second response; and subtracting the first response from the second response thereby reducing drift.

In this embodiment, the need to take a background response requirement for a baseline has been alleviated. Prior to the present invention, analyte detection required the background or ambient response to be taken as a reference. This background or reference sample is then subtracted from the test response. This method can be inefficient because the background has to be purged before an analyte can be measure. To increase the sensor array duty cycle, it has been discovered that the array of sensors can measure the analyte at two temperatures, and thereby alleviate the purge cycle. This dramatically increases sensor sampling and duty cycle. In certain aspects, the sampling is performed at two temperature values, wherein the temperature values differ between about 5° C. and about 150° C. More preferably, the temperatures differ between about 2° C. to about 70° C. In certain aspects, the analyte and the sensor array are equilibrated at the first temperature. In addition, the analyte and the sensor array are optionally equilibrated at the second temperature. In certain embodiments, the artificial olfaction device comprises two arrays of sensors.

In another aspect of differential measurements, the present invention relates to a method for reducing drift by using differential sensor measurements. Similar to thermal differences, the use of sensor arrays having various sensor thickness results in eliminating drift. Thus, in yet another embodiment, the present invention provides a method for reducing drift in an array of sensors, comprising: contacting a first sensor having a first sensor thickness with an analyte to produce a first response; contacting a second sensor having a second sensor having a second sensor thickness with the analyte at a second temperature to produce a second response; and subtracting the first response from the second response thereby reducing drift.

F. Methods to Calibrate

In general, for unequivocal characterization of their dynamic and static properties, sensors have to be calibrated and tested. In the simplest case, the calibration curve for sensor arrays is linear. The devices of the present invention provide internal diagnostics and built-in self-calibration features, which allow for improved performance. Moreover, the sensors of the present invention have the ability to perform internal diagnostics and self-calibration, thereby validating that the sensor is operating within acceptable tolerances. In certain embodiments, the devices and methods of the present invention provide the means to automatically calibrate in-situ sensor arrays, for many different analyte mixtures. The sensor calibration is routinely scheduled over an extended period at the user's discretion. In certain aspects, the devices of the present invention provide an interface to record, display and analyze sensor data in real time against an analyte standard.

II. SENSOR ARRAYS

The devices and methods of the present invention include an array of sensors and, in certain instances, the sensors as described in U.S. Pat. No. 5,571,401 are used. Sensors suitable for detection of analytes associated with agricultural products include, but are not limited to, surface acoustic wave (SAW) sensors; quartz microbalance sensors; conductive composites; chemiresitors; metal oxide gas sensors, such as tin oxide gas sensors; organic gas sensors; metal oxide field effect transistor (MOSFET); piezoelectric devices; optical sensors; sintered metal oxide sensors; Pd-gate MOSFET; metal FET structures; conducting-and nonconducting regions-disposed on metal FET structures; metal oxide sensors, such as a Tuguchi gas sensors; phthalocyanine sensors; electrochemical cells; conducting polymer sensors; catalytic gas sensors; organic semiconducting gas sensors; solid electrolyte gas sensors; temperature sensors, humidity sensors, piezoelectric quartz crystal sensors; and Langmuir-Blodgett film sensors.

In a preferred embodiment, the sensors of the present invention are disclosed in U.S. Pat. No. 5,571,401, incorporated herein by reference. Briefly, the sensors described therein are conducting materials and nonconducting materials arranged in a matrix of conducting and nonconducting regions. The nonconductive material can be a nonconducting polymer such as polystyrene. The conductive material can be a conducting polymer, carbon black, an inorganic conductor and the like. The sensor arrays comprise at least two sensors, typically about 32 sensors and in certain instances 1000 or more sensors. The array of sensors can be formed on an integrated circuit using semiconductor technology methods, an example of which is disclosed in PCT Publication WO 99/08105, entitled "Techniques and Systems for Analyte Detection," published Feb. 19, 1999, and incorporate herein by reference. Another preferred sensor is disclosed in WO 99/27357 entitled "Materials, Method and Apparatus for Detection and Monitoring Chemical Species," published Jun. 3, 1999, and incorporated herein by reference.

In one embodiment, the sensor arrays are formed from composites of poly(3,4-ethylenedioxy)thiophene-poly(styrenesulfonate) as a conductive component with an insulating polymer (see, Solzing et al., *Anal. Chem.*, 72, 3181–3190 (2000) incorporated herein by reference). The insulating polymers can be for example, poly(vinylacetate), poly(epichlorohydrin), poly(ethylene oxide), etc.

In other instances, the sensors are disclosed in WO 00/00808, published on Jan. 6, 2000, to Lewis et al. and incorporated herein by reference. Chemical sensors are disclosed comprising a plurality of alternating nonconductive regions (comprising a nonconductive material) and conductive regions (comprising a conductive material), wherein the conducting region comprises a nanoparticle.

Preferably, the sensor arrays of the present invention comprise at least one sensor selected from the following group of sensors, inorganic metal oxide semiconductors such as tin-oxide based sensors, intrinsically conducting polymers such as polymers of pyrrole, thiophene and aniline, mass sensitive piezoelectric sensors such as bulk acoustic wave and surface acoustic wave sensors, polymer compositions on metal FET, and nonconducting/conducting regions sensors.

As will be apparent to those of skill in the art, the sensors making up the array of the present invention can be made up of various sensor types as set forth above. For instance, the sensor array can comprise a conducting and nonconducting regions sensor, a SAW sensor, a metal oxide gas sensor, a conducting polymer sensor, a Langmuir-Blodgett film sensors, polymer composites on metal FET, and combinations thereof.

In certain embodiments, the temporal response of each sensor (response as a function of time) is recorded and can be displayed. Various responses include, but are not limited to, resistance, impedance, capacitance, inductance, magnetic, work function, optical, etc. The temporal response of each sensor can be normalized to a maximum percent increase and percent decrease that produces a response pattern associated with the exposure of the analyte. By iterative profiling of known analytes, a structure-function database correlating analytes and response profiles is generated. Unknown analytes can then be characterized or identified using response pattern comparison and recognition algorithms. Accordingly, analyte detection systems comprising sensor arrays, a measuring device for detecting responses across each sensor, a computer, a display, a data structure of sensor array response profiles, and a comparison algorithm(s) or comparison tables are provided. In another embodiment, the electrical measuring device or detector is an integrated circuit comprising neural network-based hardware and a digital-analog converter (DAC) multiplexed to each sensor, or a plurality of DACs, each connected to different sensor(s).

In certain embodiments, the present invention provides an array of an array of sensors. As used herein, an array of an array of sensor is termed a massively parallel independent array (MPIA). This device is a matrix of sensors that can sense multiple bottles or vessels simultaneously. The device is especially useful for assaying or for diagnostic purposes for multiple vessels. For example, in a combinatorial library of catalysts, a MPIA can be used to simultaneously determine catalysts having unique signature patterns of interest. Using the MPIA systems of the present invention it is possible to monitor the efficiency of antibiotics, catalysts, drugs, biomolecule binding efficiencies, nucleic acid hybridizations, ligand-ligand interactions, biomolecule interactions, potential drug candidates, etc. See, WO 99/53300, published Apr. 13, 1999, to Lewis et al. incorporated herein by reference. WO 99/53300 discloses chemical sensors for detecting the activity of a molecule or analyte of interest. The chemical sensors comprise an array or plurality of chemically sensitive resistors that are capable of interacting with the molecule of interest, wherein the interaction provides a resistance fingerprint. The fingerprint can be associated with a library of similar molecules of interest to determine the molecule's activity.

In one embodiment, the MPIAs of the present invention are fabricated using combinatorial techniques. Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a person of skill in the art. The nature and implementation of modifications to these devices (if any) so that they can operate as discussed herein will be apparent to skilled artisans. Moreover, combinatorial methods of making sensors are disclosed in WO 99/00663, published Jan. 7, 1999, to Lewis et al. and incorporated herein by reference. The methods disclosed therein combine various ratios of at least first and second organic materials to fabricate sensors.

The MPIA can utilize sensors as disclosed in WO 99/40423, published Aug. 12, 1999, to Lewis et al. and incorporated herein by reference. Arrays of sensors useful for analyzing chiral analytes and producing a sample output are disclosed. The array comprises compositionally different sensors, wherein a sensor comprises a chiral region. The analyte generates a differential electrical response across the sensor thereby being detected.

In certain instances, the sensor arrays comprise sensors having aligned particle based sensor elements as disclosed in WO 00/33062, published Jun. 8, 2000, to Sunshine et al. and incorporated herein by reference. The sensor arrays disclosed therein comprise first and second sensors wherein the first sensor comprises a region of aligned conductive material; electrically connected to an electrical measuring apparatus. The aligned conductive material improves the signal to noise of vapor sensors allowing lower detection limits. Such lower detection limits allow for the identification of lower concentrations of hazardous material and is advantageous in medical applications, such as the detection of disease states.

In certain other embodiments, the sensor arrays are chemically sensitive resistors wherein the resistors are composed of a conductor (e.g. carbon black) and a conducting polymer, such as polyaniline. The polyaniline composites can be used to detect biogenic amine odorants such as putrescine, cadaverine and spermine (see, Sotzing et al., *Chem. Mater.* 12, 593–595 (2000) incorporated herein by reference.).

III. PRECONCENTRATOR

In certain aspects, the present invention optionally comprises a preconcentrator. In this aspect, a volume of the gas to be sampled is introduced into a sample chamber where it is transported by means of convention, such as convection, into the vicinity of the sorbent material. Suitable transporting means include, but are not limited to, a fan, an air pump, or it can be means for heating the cylindrical container to create a convective air flow between the inlet and the outlet. The sorbent material is chosen from known materials designed for the purpose of sorbing gases, vapors, and the like. In certain embodiments, the sorbent material includes, but is not limited to, a nanoporous material, a microporous material, a chemically reactive material, a nonporous material and combinations thereof. Such absorbents include, for example, activated carbon, silica gel, activated alumina, molecular sieve carbon, molecular sieve zeolites, silicalite, $AlPO_4$, a polymer, a co-polymer, polymer blends, alumina and mixtures thereof. In certain embodiments, the absorbent has a pore size from about 1 nm to about 100 nm and, preferably, from about 1 nm to about 50 nm.

Suitable commercially available adsorbent materials are disclosed in U.S. Pat. No. 6,085,576 and include, but are not limited to, Tenax TA, Tenax GR, Carbotrap, Carbopack B and C, Carbotrap C, Carboxen, Carbosieve SIII, Porapak, Spherocarb, and combinations thereof. Preferred adsorbent combinations include, but are not limited to, Tenax GR and Carbopack B; Carbopack B and Carbosieve SIII; and Carbopack C and Carbopack B and Carbosieve SIII or Carboxen 1000. Those skilled in the art will know of other suitable absorbent materials.

After sometime period that is chosen to be adequate for sorbing the desired analytes from the vapor phase onto the material, the circulation is stopped and then the material is desorbed from the sorbent phase and released into the sensor chamber. The desorbing of the concentrated analyte from the sorbent can be accomplished by thermal means, mechanical means or a combination thereof. Desorption methods include, but are not limited to, heating, purging, stripping, pressuring or a combination thereof.

In certain embodiments, the sample concentrator is wrapped with a wire through which current can be applied to heat and thus, desorb the concentrated analyte. The analyte is thereafter transferred to the sensor array.

The process of sorbing the material onto the sorbent phase not only can be used to concentrate the material, but also can be advantageously used to remove water vapor. The water vapor is preferably removed prior to concentrating the analyte; however, in various embodiments, the vapor can be removed concomitantly or after the analyte is concentrated. In a preferred embodiment, the water vapor is removed prior to presenting the desired analyte gas mixture to the sensor array. Thus, in certain embodiments, the fluid concentrator contains additional absorbent material to not only concentrate the analyte, but to remove unwanted materials such gas contaminates and moisture.

IV. ALGORITHMS

The device and methods of the present invention optionally comprise pattern recognition algorithms. Many of the algorithms are neural network based algorithms. A neural network has an input layer, processing layers and an output layer. The information in a neural network is distributed throughout the processing layers. The processing layers are made up of nodes that simulate the neurons by its interconnection to their nodes.

In operation, when a ANN is combined with a sensor array, the sensor data is propagated through the networks. In this way, a series of vector matrix multiplications are performed and unknown analytes can be readily identified and determined. The neural network is trained by correcting the false or undesired outputs from a given input. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In a preferred embodiment, the Fisher linear discriminant analysis (FLDA) and canonical discriminant analysis (CDA) and combinations thereof are used to assess patterns in responses from the electronic noses of the present invention. Operating principles of various algorithms suitable for use in the present invention have been disclosed (see, Shaffer et al., *Analytica Chimica Acta*, 384, 305–317 (1999)). The Fisher linear discriminant analysis as it pertains to artificial olfaction is disclosed in WO 99/61902, published Dec. 2, 1999, to Lewis et al., and incorporated herein by reference.

V. NETWORKED SYSTEMS

In certain instances, the devices, methods and apparatus of the present invention can be used in a networked environment. For instance, the networked systems of the present invention allow the methods to be carried out in one location such as with a handheld device and subsequently transmit digital signals over a computer network, such as the Internet, for analysis at a remote location. Suitable methods and systems for detecting and transmitting sensory data over a computer networked are disclosed in WO 00/52444, published Sep. 8, 2000, to Sunshine et al. and incorporated herein by reference.

As disclosed therein, communication between the on-board processor of an artificial olfaction device and the host computer is available to configure the device and to download data from or to the outside world, in real time or at a later time via a number of communication interfaces including, but not limited to, an RS-232 interface, a parallel port, an universal serial bus (USB), an infrared data link, an optical interface and an RF interface. Serial communications to the outside world are provided by the on-board low power RS-232 serial driver. Communication to the outside world includes, but is not limited to, a network, such as a computer network e.g. the Internet accessible via Ethernet, a wireless Ethernet, a token ring, a modem, etc. A transfer rate of 9600 bits/second can transmit approximately 400 data points/second, and higher transfer rates can be used.

The computer network can be one of a variety of networks including a worldwide computer network, an Internet, the Internet, a WAN, a wireless network, a LAN or an intranet. It should be understood that conventional access to the computer network is conducted through a gateway. A gateway is a machine, for example, a computer that has a communication address recognizable by the computer network.

VI. EXAMPLES

The following examples are offered to illustrate, but not to limit the claimed invention.

Example 1

This Example illustrates an e-nose device having two sensor arrays wherein sensor element 2 has a porous membrane associated therewith.

In this Example, the detection and identification of analytes will be accomplished by using an electronic nose having two 32-sensor arrays. Sensor element 1 (having 32-sensors) is a sensing array and sensor element 2 (having 32-sensors) is a referencing array. Sensor element 2 has a porous membrane associated therewith. The analyte's contact with the reference sensor array will thus be slowed. The porous membrane limits diffusion to the 2nd sensor. This process of limited diffusion of the analyte allows sampling of the sensors at different points of time and thus, referencing and calibration can be done simultaneously.

A Keithley electrometer and scanner will be used to scan the resistances of two 32-sensor arrays during the experiment. In certain instances, the temperature of the substrates will not be controlled and the measurements will be done at room temperature. For each sample test, there will be 60 seconds of background recording (purged with air), 120 seconds of exposure time, 120 seconds of recovery time (purged with air with RH level of about 3%), 180 seconds of recovery without recording the data (purged with air), and 30 seconds of final recording time (purged with air).

The response patterns from the two 32-sensor array will have good reproducibility. The response (the normalized resistance change, $(R_{max}-R_o)/R_o$), where $R_{max}$ and $R_o$ are the maximum and base (initial) resistance, respectively) of each of the sensor arrays to each sample tested will be employed to form a covariance matrix, which is used to do principal component analysis. PCA of the analytes plus control will be clearly discriminated by the sensor array. SIMCA is also used to evaluate the data.

Figure 8:
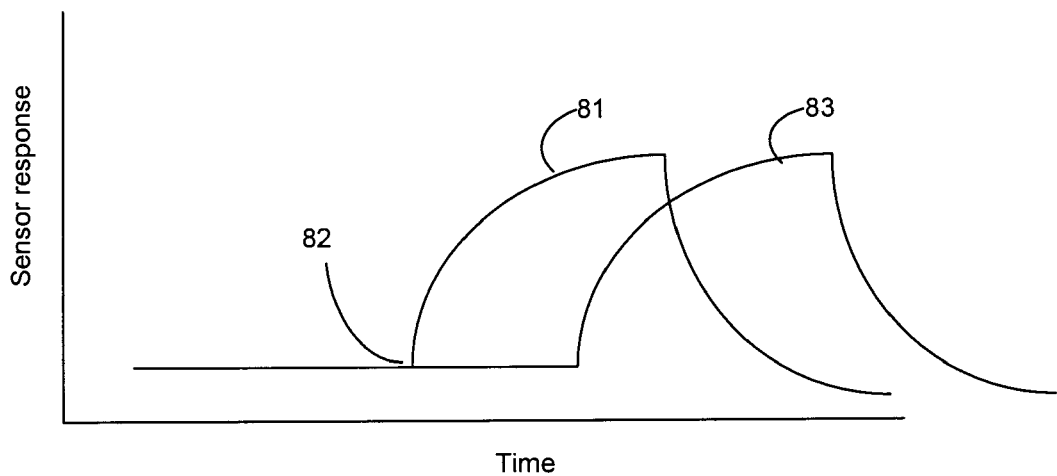
FIG. 8 illustrates a sensor response using a device of the present invention.

As shown in FIG. 8, the sensor response 81 at time $t_1$ where the first sensor is just beginning to respond 82 will give a $\Delta R/R$ value and the second sensor array will give a second response 83. The two individual $\Delta R/R$ values (for the first and second trace) can be used to calibrate the system. The sensor arrays are identical and therefore, the two responses are identical. The pasivation material on the second sensor only slows diffusion and is not selective.

Example 2

This Example illustrates differential temperature measurement of sensor arrays.

In this method an analyte is detected at two temperatures. The first sampling is conducted at ambient temperature and the second temperature is at 60° C. In this experiment, the drift of the sensor array can be reduced using differential thermal measurements. Thus, by contacting the array of sensor with an analyte at a first temperature to produce a first response and subsequently contacting the array of sensors with the analyte at a second temperature to produce a second response and thereafter, subtracting the first response from the second response the drift can be reduced. Thus, the need to take a background response has been alleviated. Using this method, dramatic increases in sensor sampling and duty cycle are achieved.

Example 3

This Example illustrates the use of a massively parallel independent array (MPIA) to monitor a reaction such as the conversion of one reactant to another using a combinatorial library of catalysts. The method is a way of evaluating catalyst activity.

A different catalyst is loaded into small wells of a microtiter plate (e.g., 96-well or 384-well microtiter plates) together with the target reactants. In certain aspects, the catalysts are prepared using combinatorial techniques. Such catalysts include for instance, palladium on carbon (having various weight percents of palladium e.g., 1%, 2%, 3%, etc.), Raney nickel, Raney copper, etc. The MPIA is mounted on the headspace of the microtiter plate for real time monitoring of the conversion process related to catalytic activity. In a preferred embodiment, above each well in the microtiter plate, is a sensor array (i.e., at least two sensors). Thus, in certain aspects, such as in a 96 well format, there are at least 192 total sensors in the MPIA. In a 384 format, there are in certain aspects, at least 768 sensors in the MPIA.

Specific examples of catalytic activity include, but are not limited to, the hydrogenation of 1-hexyne to 1-hexene or to hexane (i.e. the fully saturated hydrocarbon) using a variety of oxides as the catalysts. The decrease in 1-hexyne concentration and the increase in concentration of the saturated hydrocarbons can be monitored using the sensor array(s) and analyzed with a computer in real time. Complete conversion of the 1-hexyne can also be determined.

Another specific example includes the dehydrogenation of cyclohexane to benzene using a library of solid-state catalysts. The decrease in cyclohexane concentration and the increase in benzene concentration can be monitored using a sensor array(s) and the conversion monitored real time.

Advantageously, independent response patterns for each sensor array are simultaneously monitored and compared. Thus, using the MPIA in a 96-well format of the present invention, sensor array above well 1–96 is compared with sensor array 33–96 and so forth. Thus, each sensor array within the MPIA (1–96, 2–96, 3–96, 4–96, etc.) is simultaneously and independently monitored. In operation, a matrix of response patterns is generated and compared using pattern recognition algorithms. In certain aspects, the efficiency of the reactions is monitored in real time. Preferably, the MPIA system resides in a networked environment. Using the MPIA systems of the present invention it is possible to monitor the efficiency of antibiotics, catalysts, drugs, biomolecule binding efficiencies, nucleic acid hybridizations, ligand-ligand interactions, biomolecule interactions, drug candidates, etc.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for reducing drift in an artificial olfaction device having an array of sensors, said method comprising:

contacting said array of sensor with an analyte at a first parameter selected from the group consisting of temperature, pressure and humidity to produce a first response;

contacting said array of sensor with said analyte at a second parameter selected from the group consisting of temperature, pressure and humidity to produce a second response; and measuring the differential response, then referencing the differential response to the first and second responses of the sensor array to reduce drift in the sensor array to thereby reduce drift.

2. The method of claim 1, wherein at least one sensor in said array of sensors in selected from the group consisting of a conducting and nonconducting regions sensor, a SAW sensor, a quartz microbalance sensor, a conductive composite sensor, a chemiresitor, a metal oxide gas sensor, an organic gas sensor, a MOSFET, a piezoelectric device, an infrared sensor, a sintered metal oxide sensor, a Pd-gate MOSFET, a metal FET structure, a electrochemical cell, a conducting polymer sensor, a catalytic gas sensor, an organic semiconducting gas sensor, a fiber optical chemical sensor, a solid electrolyte gas sensors, and a piezoelectric quartz crystal sensor.

3. The method of claim 2, wherein at least one sensor is a conducting and nonconducting regions sensor.

4. The method of claim 2, wherein at least one sensor is a SAW sensor.

5. The method of claim 1, wherein said analyte and said sensor array are equilibrated at said first temperature.

6. The method of claim 1, wherein said analyte and said sensor array are equilibrated at said second temperature.

7. The method of claim 1, wherein the difference between said first temperature and said second temperature is between about 5° C. and about 150° C.

8. The method of claim 7, wherein the difference between said first temperature and said second temperature is between about 2° C. to about 70° C.

9. The method of claim 1, wherein said artificial olfaction device comprises two arrays of sensors.

10. The method of claim 1, wherein said artificial olfaction device is a handheld device.

11. The method of claim 1, wherein the differential response is measured by subtracting the first response from the second response.

12. The method of claim 1, wherein the parameter is temperature.

13. The method of claim 1, wherein the parameter is pressure.

14. The method of claim 1, wherein the parameter is humidity.

* * * * *